(12) United States Patent
Augustine et al.

(10) Patent No.: US 7,381,471 B2
(45) Date of Patent: Jun. 3, 2008

(54) HYBRID POLYMERS FOR FUNCTIONAL TUNING OF MICROFLUIDIC DEVICE SURFACES

(75) Inventors: Brian H. Augustine, Bridgewater, VA (US); James P. Landers, Charlottesville, VA (US); Jerome P. Ferrance, Charlottesville, VA (US); Joy M. Polefrone, Charlottesville, VA (US); W. Christopher Hughes, Harrisonburg, VA (US)

(73) Assignees: University of Virginia Patent Foundation, Charlottesville, VA (US); James Madison University, Harrisonburg, VA (US)

( * ) Notice: Subject to any disclaimer, the term of this patent is extended or adjusted under 35 U.S.C. 154(b) by 503 days.

(21) Appl. No.: 10/520,763

(22) PCT Filed: Jul. 15, 2003

(86) PCT No.: PCT/US03/22162

§ 371 (c)(1),
(2), (4) Date: Jan. 10, 2005

(87) PCT Pub. No.: WO2004/007582

PCT Pub. Date: Jan. 22, 2004

(65) Prior Publication Data

US 2006/0057402 A1    Mar. 16, 2006

Related U.S. Application Data

(60) Provisional application No. 60/399,633, filed on Jul. 30, 2002, provisional application No. 60/396,153, filed on Jul. 15, 2002.

(51) Int. Cl.
*B32B 25/20* (2006.01)
(52) U.S. Cl. ...................... 428/447; 428/451
(58) Field of Classification Search ............ 428/447, 428/451
See application file for complete search history.

(56) References Cited

U.S. PATENT DOCUMENTS

| 4,510,257 | A | 4/1985 | Lewis et al. | |
|---|---|---|---|---|
| 5,376,252 | A | 12/1994 | Ekström et al. | |
| 5,561,208 | A | 10/1996 | Takahashi et al. | |
| 6,326,083 | B1 | 12/2001 | Yang et al. | |
| 6,425,936 | B1* | 7/2002 | Sammons et al. | 95/45 |
| 6,558,455 | B2 | 5/2003 | Sammons et al. | |
| 6,576,345 | B1 | 6/2003 | Van Cleemput et al. | |
| 6,586,548 | B2 | 7/2003 | Bonafini, Jr. et al. | |
| 6,653,365 | B2 | 11/2003 | Jia | |
| 2002/0029968 | A1 | 3/2002 | Tan et al. | |
| 2002/0128414 | A1 | 9/2002 | James, Jr. et al. | |
| 2002/0182541 | A1 | 12/2002 | Gonsalves | |

FOREIGN PATENT DOCUMENTS

| EP | 1 036 808 A2 | 9/2000 |
|---|---|---|
| EP | 1 036 808 B1 | 12/2002 |
| WO | WO 01/72885 A1 | 10/2001 |
| WO | WO 02/08744 A2 | 1/2002 |

OTHER PUBLICATIONS

Chen, Y.-H., et al., (2000). "Analysis of DNA fragments by microchip electrophoreses fabricated on poly(methylmethacrylate) substrates using a wire-imprinting method", Electrophoresis, vol. 21, pp. 165-170.
Dang, F., et al., (2003). "Ultrafast analysis of oligosaccharides on microchip with light-emitting diode confocal fluorescence detection", Electrophoresis, vol. 24, pp. 714-721.
Galloway, M., et al., (2002). "Contact Conductivity Dectection in Poly(methylmethacylate)-Based Microfluidic Devices for Analysis of Mono- and Polyanionic Molecules", Anal. Chem., vol. 74, pp. 2407-2415.
Grass, B., et al., (2001). "A new PMMA-microchip device for isotachophoresis with integrated conductivity detector", Sensors and Sctuators B, vol. 72, pp. 249-258.
Lee, G.-B., et al., (2001). "Microfabricated plastic chips by hot embossing methods and their applications for DNA separation and detection", Sensors and Actuators B, vol. 75, pp. 142-148.
Lichtenhan, J.D., et al., (1995). "Linear Hybrid Polymer Building Blocks: Methacrylate-Funtionalized Polyhedral Oligomeric Silsesquioxane Monomers and Polymers", Macromolecules, vol. 28, pp. 8435-8437.
Lin, Y.-C., et al., (2001). "Electroporation microchips for continuous gene transfection", Sensors and Actuators B, vol. 79, pp. 137-143.

(Continued)

*Primary Examiner*—Kuo-Liang Peng
(74) *Attorney, Agent, or Firm*—Rodney L. Sparks

(57) ABSTRACT

The present invention is directed to improved microdevices and methods of manufacturing such devices. More particularly the present invention is directed to the use of a compound having the general structure (formula (I)): wherein R is selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl for bonding silica based substrates to plastic substrates or to other silica based substrates. In addition the polymer can be used to coat microchannels to enhance the physical properties of the microdevice

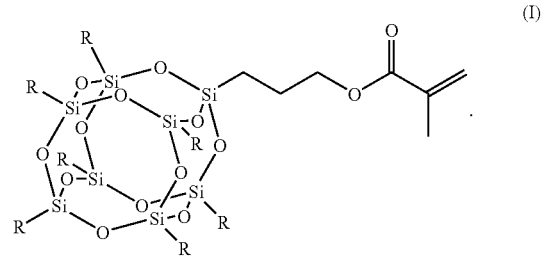

19 Claims, 2 Drawing Sheets

OTHER PUBLICATIONS

Soper, S.A., et al., (1999). "Nanoliter-scale sample preparation methods directly coupled to polymethylmethacrylate-based microchips and gel-filled capillaries for the analysis of oligonucleotides", J. of Chromatography A, vol. 853, pp. 107-120.

Sung, W.-C., et al., (2001). "Plastic microchip electrophoresis for genetice screening: The analysis of polymerdase chain reactions products of fragile X(CGG)n alleles", Electrophoresis, vol. 22, pp. 1188-1193.

Wang, J., et al., (2002). "Towards disposable lab-on-a-chip: Poly(methylmethacrylate) microchip electrophoresis device with electrochemical detection", Electrophoresis, vol. 23, pp. 596-601.

Xu, F., et al. (2002). "DNA Separation by microchip electrophoresis using low-viscosity hydroxypropyl-methylcellulose-50 solutions enhanced by polyhydroxy compounds", Electrophoresis, vol. 23, pp. 3608-3614.

Zhang, W., et al., (2002). "Effect of Methyl Methacrylate/Polyhedral Oligomeric Silsesquioxane Random Copolymers in Compatibilixation of Polystyrene and Poly(methyl methacrylate) Blends", Macromolecules, vol. 35, pp. 8029-8038.

Pumera, M., et al., (2002). "Contactless Conductivity Detector for Microchip Capillary Electrophoresis", Anal. Chem., vol. 74, pp. 1968-1971.

* cited by examiner

HYBRID POLYMERS FOR FUNCTIONAL TUNING OF MICROFLUIDIC DEVICE SURFACES

RELATED APPLICATION

This application is a national stage filing of International Application No. PCT/US03/22162, filed on Jul. 15, 2003, which claims benefit under 35 USC §119(e) to U.S. Provisional Application Ser. Nos. 60/396,153, filed Jul. 15, 2002, and 60/399,633, filed Jul. 30, 2002, the disclosures of which are incorporated herein by reference in their entirety.

BACKGROUND

Miniaturization of analytical methods and instrumentation for biomedical and clinical research is an area of burgeoning interest. In many cases, the reduction in size of an analytical procedure or technique often translates to a reduction in analysis time and costs. Miniaturization of analytical methods often paves the way for the use of established technologies in high-throughput applications. Accordingly, microchips have been developed for many applications in order to minimize both the time and space required to perform processes such as drug delivery and clinical diagnostic procedures. Furthermore, the use of microchips is ideal due to the ability to perform rapid separations using small analyte volumes and parallel processing in these devices.

Great efforts have been made to develop fast, cost-effective, high-throughput separation methods for nucleic acid analysis. For example, microchip technology is currently being developed in which rapid thermocycling and electrophoretic separation can be accomplished 10 times quicker than conventional techniques. The microchip platform has the potential for integrating sample pretreatment, target amplification, and detection in a single device. Microfabricated chips have also been developed for electrophoretic separations of nucleic acids and proteins. It has been reported that electrophoretic microchips can be used for separation and sensitive laser-induced fluorescence (LIF) detection, with a variety of clinically-relevant analytes, without loss of diagnostic information relative to procedures conducted with traditional slab-gel electrophoresis.

One advantage of electrophoretic microchips is the ability to move fluids through the chip architecture with nothing more than an applied potential. In addition, directional fluid flow at intersections can be electrokinetically-valved by applying potentials to the correct locations in the microchip. These phenomena are, at least in part, controlled by electroosmotic flow.

Electroosmotic Flow (EOF)

The most commonly used substrate for microchips is glass, due to both its optical properties and the ability to use standard photolithographic techniques to fabricate microstructures. In many ways, glass is an ideal substrate for electrophoretic microchips. It is a good electrical insulator localizing the fields used for electrophoretic separation to the microchannel structures where the separation is to occur. Furthermore, the chemical composition of glass, a mixture of siloxanes and silanol groups, allows for electroosmotic flow (EOF) under the appropriate conditions. EOF is essentially an electric field-driven pumping that generates "bulk flow" as a result of the fact that the silanols on the glass surface can be deprotonated. This produces a negatively-charged wall which, in the presence of a low ionic strength buffer, induces the formation of a double layer of cations (the double electric layer, see FIG. 1); this generates a potential at the surface termed the "zeta ($\xi$) potential". Under low ionic strength conditions, in properly sized channels, application of an electric field induces movement of the double layer, generating a bulk-flow within the channel. This phenomenon is described by the formula:

$$\mu_{EOF} = \xi \epsilon / \eta \qquad \text{(eq. 1)}$$

where $\mu_{EOF}$ is the mobility of the bulk flow, $\xi$ is the zeta-potential on the surface of the capillary or microchannel wall, $\epsilon$ is the dielectric constant of the medium and $\eta$ the viscosity of the medium.

The $pK_a$'s of the silanol groups present on the surface of glass substrates are typically between 3 and 8, depending upon the makeup of the glass. This means that the surface charge and, thus, the zeta potential, are affected by the pH of the solution in contact with the wall. Above pH 9, all silanol groups are deprotonated, but in lower pH solutions the surface charge decreases as the pH decreases. The greater the extent of deprotonation of the silanol groups, the higher the $\xi$-potential and the greater the magnitude of the EOF. In contrast, at low pH (e.g., pH 2), the silanols are completely protonated, the negative charge on the surface is negligible, the $\xi$-potential is very small and the EOF approaches zero.

The magnitude of the EOF is not only a function of the pH, it is also dependent on the ionic strength of the solution contacting the surface. The ionic strength impacts the thickness of this diffuse layer extending into the lumen of the capillary/microchannel, with the thickness being inversely proportional to the square root of the ionic strength of the solution. Hence, as the ionic strength decreases, the diffuse layer thickness increases and so does the magnitude of the EOF. An approximate thickness for the diffuse layer can be as small as 5-10 Å for an electrolyte concentration of 100 mM, up to a distance of 50-100 nm for an electrolyte concentration of 1 mM. Consequently, EOF magnitude is typically inversely proportional to the buffer concentration.

While glass has many advantages as a substrate for microfluidic devices, there are also drawbacks to the use of glass. The premier disadvantages include: 1) limited control of EOF, 2) thermal properties, 3) surface passivation needed for many applications, and 4) high temperature bonding. The EOF problem arises, as it is often necessary to control the magnitude of EOF to perform successful separations. For example, DNA separations require an EOF as close to zero as possible, where as the separation of carbohydrates requires an adequate EOF. Unfortunately, the main parameters for controlling EOF (pH and ionic strength) cannot always be "dialed in" to generate the requisite EOF because they may not be compatible with the conditions needed for separation of the analytes or for analyte stability. Consequently, there has been an on-going search for controlling EOF with means other than pH and ionic strength.

The thermal properties of glass make it ideal for electrophoretic separation, where Joule heating of the solution, due to the current in the capillary or channel, must be minimized. These same properties become problematic however for some of the desired functionalities that can be integrated into microchips. For example, thermal cycling for polymerase chain reaction (PCR) amplification of DNA is now carried out on microchips. The ability to remove heat from the solution, and the inability to rapidly cool the glass microchip prohibits the ultrafast heating and cooling rates that can be achieved on plastic substrates. This leads to longer cycling times and extends the time required to complete the PCR. In addition, passivation of the glass surface is also a problem with a number of biologically-active molecules. Proteins, in particular, have a proclivity for binding to the charged surface of glass as well as other substrate surfaces. This is problematic with protein separation, as well as with the microchip PCR amplifications. PCR is an enzymatic process driven by *Thermus aquaticusis* (Taq) polymerse, which can be adsorbed to the surface and inhibit its function.

Fabrication of glass microdevices also presents some problems. While clear-cut protocols exist for wet etching of microstructures into glass, bonding of a glass coverplate plate to an etched glass substrate is less straight-forward. Glass microchips are typically bonded using a procedure that includes heating the glass to temperatures as high as 695° C. to fuse the two glass surfaces. The silanols in the channel become dehydrated at these high temperatures, and the surface characteristics have changed enough that EOF is often not seen unless the surface is extensively treated (strong acid or base) to restore the siloxane groups. Even then, coating of the surface with an ionic polymer is sometimes used to ensure consistent reproducible EOF in microfluidic channels. The thermal bonding process is time consuming, requiring an annealing process in excess of eight hours, and often requires repeated bonding cycles. Because different glasses have different expansion properties, high temperature thermal bonding requires the etched plate and coverplate be prepared from the same glass. This is not always optimal for devices, as different etching properties, optical properties, or available thickness may be desired for the two substrate plates to be bonded. Moreover, the extreme temperatures required for bonding preclude the incorporation of additional features during the manufacturing process. These would include metals, which could be used for electrodes integrated directly into the devices, or any coatings or polymeric structures, which might be desired for passivating or "tuning" the surface in the etched features of the microfluidic devices.

Low temperature bonding processes have been proposed for glass devices, but those procedures require perfectly flat glass, and scrupulous cleaning of the surfaces to be bonded. A second method utilizes sodium silicate materials spin-coated onto the etched surface of the glass wafer. The coverplateplate is then put in place and the assembly heated to 90° C. to cure the silicate adhesive. This method has not been widely used because of the difficulties in preparing and using the sodium silicate solutions.

Other Microdevice Materials

While glass is the predominant material used for electrophoretic microdevices, plastic materials offer advantages in terms of cost and ease of fabrication. Plastics are relatively inexpensive to manufacture, using techniques such as hot embossing or injection molding. This allows the production of disposable devices, which would be beneficial for many applications. There are a number of plastics from which to choose, and bonding can be carried out at relatively low temperatures. Disadvantages associated with plastic microdevices include the optical properties, with some polymeric materials having intrinsic fluorescence and others not being optically clear in the wavelengths of interest. In particular, many plastics absorb in the UV wavelengths, which are important either for absorbance measurements or excitation of many fluorescent compounds. A more important problem is that the surface of the plastics is not well suited for the production of EOF. The surface within the channel must then be treated to provide a surface amenable to formation of the double layer needed for EOF generation.

SUMMARY OF EMBODIMENTS

The present invention is directed to improved silica-based microchip devices and methods of manufacturing such devices. In one embodiment a method is provided for manufacturing hybrid microchips that comprises glass and plastic components fused together through the use of a PMMA-POSS polymer. In another embodiment, the present invention comprises a microchip device whose internal surfaces have been coated with a POSS™ containing polymer to enhance the physical properties of the device.

DETAILED DESCRIPTION OF EMBODIMENTS OF THE INVENTION

Definitions

Figure 1:
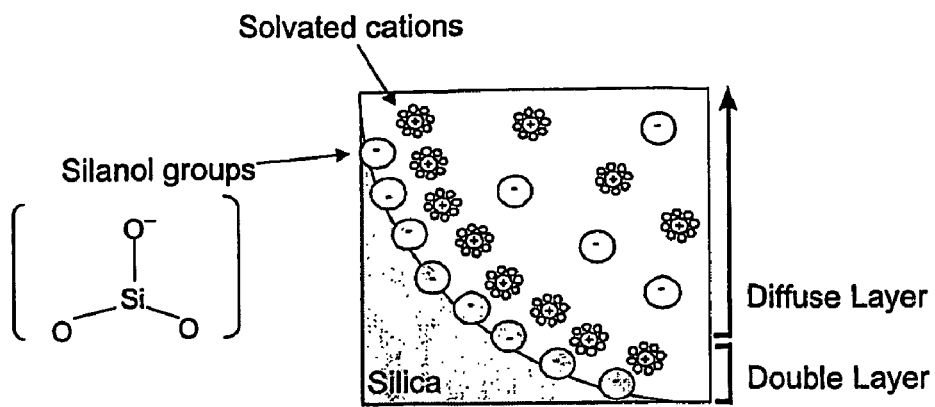
FIG. 1: Effectors of EOF in a Silica Capillary. Solvated cations form a double layer with the negatively charged surface silanol groups. Beyond this double layer, a more diffuse layer continues into the lumen of the capillary. Thickness of the diffuse layer is dependent upon the ionic strength of the electrolyte and ranges roughly between 5 Å to 100 nm.

In describing and claiming the invention, the following terminology will be used in accordance with the definitions set forth below.

The general chemical terms used in the description of the compounds of the present invention have their usual meanings. For example, the term "alkyl" by itself or as part of another substituent means a straight or branched aliphatic chain having the stated number of carbon atoms.

The term "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, refers to a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer, refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_1$-$C_4$ alkoxy" as used herein represents a group of the structure —OR wherein O is oxygen and R is $C_1$-$C_4$ alkyl. Examples of such groups include, but are not limited to, methoxy, ethoxy, n-propoxy, isopropoxy, t-butoxy, n-pentoxy and n-hexoxy.

The term "carboxyl" herein refers to —$CO_2H$.

The term "sulfate" includes a moiety represented by the general formula:

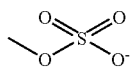

As used herein, the term "optionally substituted" refers to zero to four substituents, wherein the substituents are each independently selected.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. Substituted aryl includes aryl compounds having one or two $C_1$-$C_6$ alkyl, halo or amino substituents. The term (alkyl)aryl refers to any aryl group which is attached to the parent moiety via the alkyl group.

The term "$C_3$-$C_n$ cycloalkyl" wherein n=4-8, represents cyclopropyl, cyclobutyl, cyclopentyl, cyclohexyl, cycloheptyl, and cyclooctyl.

The term "heterocyclic group" refers to a $C_3$-$C_8$ cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "chaotropic agent" as used herein is an agent that is capable of disrupting the membranes or other structural components of living organisms and includes but is not limited to urea, guanidine hydrochloride, potassium iodine, enzymes such as lysozyme, alkali solutions, chelators such as EDTA and EGTA and detergents such as SDS, Tween, TritonX and Sarkosyl.

As used herein, the term "immobilization" refers to the attachment or entrapment, either chemically or otherwise, of material to another entity (e.g., a solid support) in a manner that restricts the movement of the material.

As used herein a "microchannel" is a passageway (in any form, including a closed channel, a capillary, a trench, groove or the like) formed on or in a microfluidic substrate (a chip, bed, wafer, laminate, or the like) having at least one region with a cross sectional dimension selected from a range of about 50 mm$^2$ to about 100 μm$^2$.

A "microfluidic device" as used herein is an apparatus or component of an apparatus that includes at least one microchannel.

As used herein, the term "silica based substrate" or "silica based composition" refers to preparations comprising silica, and include fused silica, glass, quartz and other bonded networks of silica.

As used herein, the term "coating" refers to an application of an amount of material in a conformally and contiguous layer that is sufficient to either enhance electroosmotic flow or reduce interactions between the coated substrate and solutes in contact with the coating. As used herein a "coating" does not imply that the applied material is uniform in thickness across the entire coated surface.

As used herein, a POSS copolymer is a polymer formed by polymerizing a mixture comprising a POSS™ monomer of the general structure:

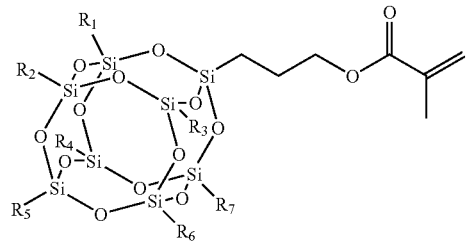

wherein R, $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkyl$(NR_{21}R_{22})$, $C_1$-$C_8$ alkyl $(NHR_{22})$, $C_1$-$C_8$ alkylsulfate, $C_3$-$C_8$ cycloalkyl, and $C_5$-$C_6$ aryl, with at least one additional monomer, wherein the additional monomer(s) is capable of polymerizing with said POSS™ monomer.

A "hybrid device" as used herein refers to a device comprising two different components bonded to one another via a POSS copolymer. The two different components are each comprised of different materials relative to one another (or at least the structure of the material comprising the two components differs). For example the hybrid device may comprise a glass component bonded to a plastic component or two glass components, having different thermal expansion properties, are bound to one another.

Embodiments

There is a strong desire to discover methods for easing the fabrication and enhancing the utility of analytical microdevices. The availability of new substrates, new bonding methods, and novel approaches for controlling the surface of the structures within these devices offer great promise for producing such improved devices. The present invention describes a novel method for improving the functionality of microdevices as well as improving the methods of preparing such devices. In accordance with one embodiment a hybrid inorganic-organic nanocomposite thin film polymeric material is used in the fabrication of microdevices.

The polymers used in the present invention are derived from a class of chemicals known as polyhedral oligomeric silsesquioxanes (POSS). POSS™ has two unique features:

(1) the chemical composition is a hybrid, intermediate (RSiO$_{1.5}$) between that of silica (SiO$_2$) and silicones (R$_2$SiO). (2) POSS™ molecules are physically large, ranging from approximately 1-3 nm. POSS™ materials are thermally and chemically more robust than silicones and their nanostructured shape and size provide unique properties by controlling polymer chain motion at the molecular level. POSS™ molecules are extremely tailorable, permitting a wealth of new nanostructured materials to be designed and synthesized from the bottom up. In accordance with one embodiment the polymer coatings used in the improved microdevices of the present invention comprise POSS copolymers. In one embodiment the polymer coatings comprise Poly(piropylmethacryl Isobutyl Polyhedral Oligomeric Silsesquioxanes™-co-methylmethacrylate) or PMMA-POSS. PMMA-POSS and related compounds are commercially available from Hybrid Plastics, (18237 Mt. Baldy Circle, Fountain Valley, Calif. 92708-6117). The general structure of the PMMA-POSS monomer form is as follows:

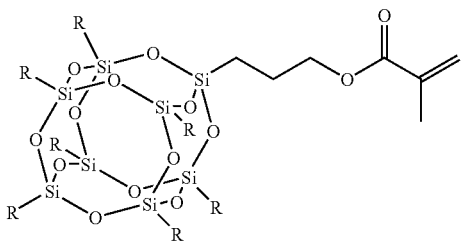

wherein R is selected from the group consisting of C$_1$-C$_{18}$ alkyl, C$_2$-C$_{18}$ alkenyl, C$_2$-C$_{18}$ alkynyl, C$_1$-C$_8$ alkylcarboxyl, C$_1$-C$_8$ alkylsulfate, C$_1$-C$_8$ alkyl(NR$_{20}$R$_{21}$R$_{22}$)$^{30}$, C$_3$-C$_8$ cycloalkyl, and C$_5$-C$_6$ aryl, wherein R$_{20}$, R$_{21}$ and R$_{22}$ are independently selected from the group consisting of H and C$_1$-C$_4$ alkyl.

The choice of this nanocomposite was based on the properties of the separate components. Preferably, the polymer used should have desirable optical properties including transparency well into the UV region with a low absorption edge. Polymers with low fluorescence emission are desirable to allow for detecting electrophoretic bands by fluorescence emission. The POSS™ functionality was chosen to potentially aid in bonding of the polymer to silica substrates due to the presence of the hydrophilic siloxal groups in the structure. In accordance with one embodiment, polymethylmethacrylate (PMMA) was chosen for copolymerization with POSS™ since it is transparent well into the UV region and has an absorption edge as low as 230 nm. However other polymers can be use as copolymers with POSS™ including for example, polycarbonate, polyethylene terephthalate and cyclic olefin homopolymer or copolymer thermoplastics derived from ring-shaped norbornene molecules. The latter polymers, such as described in U.S. Pat. Nos. 5,561,208, 5,462,995, and 5,334424, are characterized by very low fluorescence emission, and thus are suitable for detecting electrophoretic bands by fluorescence emission. Preferred polymers of this type include Zeonex and Zeonor tradename polymers, such as Zeonor 1420, manufactured by Zeon Corporation (Louisville, Ky.).

In accordance with the present invention a microfluidic device is provided wherein at least one surface is coated with a polymer produced by polymerizing a POSS™ monomer of the general structure

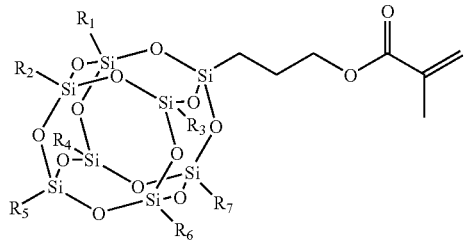

wherein R$_1$, R$_2$, R$_3$, R$_4$, R$_5$, R$_6$, and R$_7$ are independently selected from the group consisting of C$_1$-C$_6$ alkyl, C$_2$-C$_6$ alkenyl, C$_2$-C$_6$ alkynyl, C$_3$-C$_8$ cycloalkyl, and C$_5$-C$_6$ aryl, with methylmethacrylate or other suitable monomer that generates a transparent polymer with a low absorption edge. Accordingly, in one embodiment the POSS™ monomer is copolymerized with methylmethacrylate, or with polycarbonate or polyethylene terephthalate (PET) monomers, or any combination thereof. The resultant copolymers of the present invention comprise about 10 wt % to about 80 wt % of the POSS™ subunit. In one embodiment the R$_1$, R$_2$, R$_3$, R$_4$, R$_5$, R$_5$, and R$_7$ substituents of POSS™ are all identical, and in another embodiment the R$_1$, R$_2$, R$_3$, R$_4$, R$_5$, R$_6$, and R$_7$ substituents of POSS™ are independently selected from the group consisting of C$_1$-C$_4$ alkyl, C$_5$-C$_8$ cycloalkyl and C$_5$-C$_6$ aryl, and in a further embodiment the R$_1$, R$_2$, R$_3$, R$_4$, R$_5$, R$_6$, and R$_7$ substituents of POSS™ are all identical and selected from the group consisting of tert-butyl, cyclopentyl, cyclohexyl and phenyl.

The composition of the copolymeric material of the present invention is such that its properties can be modified by controlling the percentage of POSS™ incorporated during the polymerization reaction. In conjunction with the presence of the hydrophilic side groups on the POSS copolymer, controlling the concentration of POSS™ in the nanocomposite material will determine the hydrophobicity of the resulting polymer. Pure PMMA is very hydrophobic, but the POSS™ comonomer can be combined with it ranging anywhere from about 10 wt % to about 80 wt % POSS™ and more typically ranging from about 20 wt % to about 70 wt %, and all points between as a means of introducing hydrophilicity into the polymer.

Figure 2:
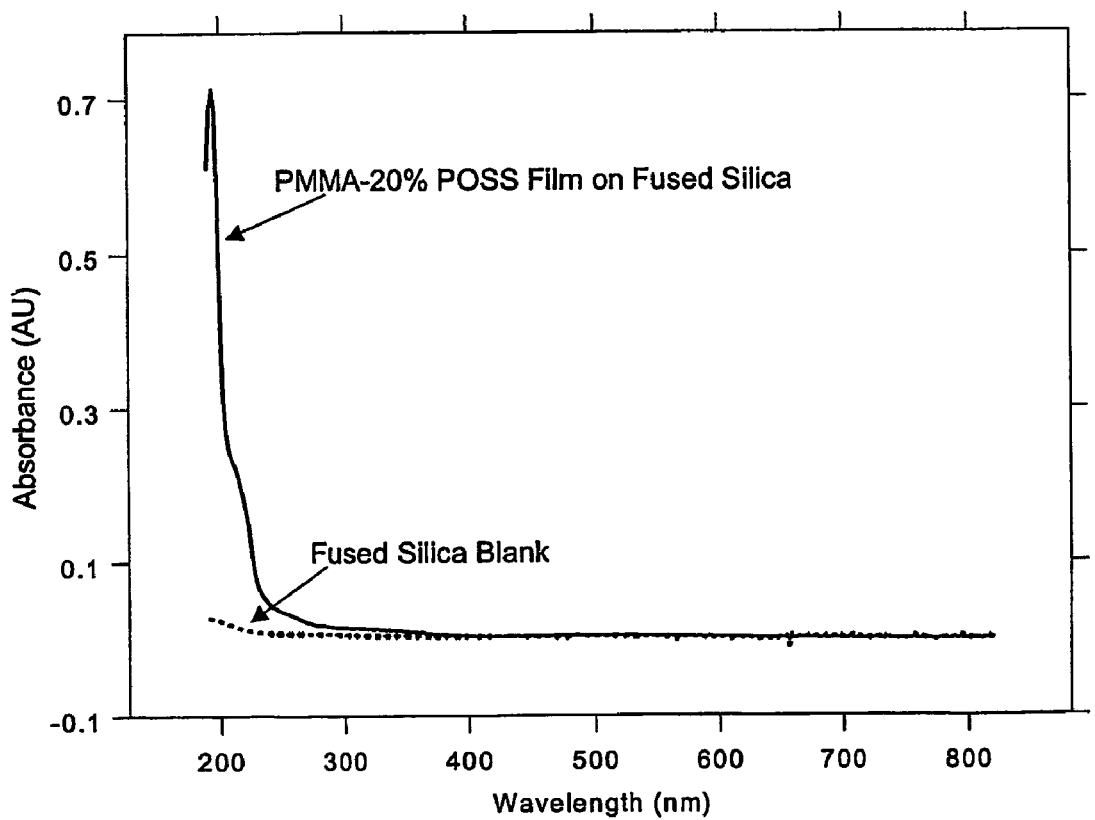
FIG. 2. Absorbance spectra of PMMA-POSS 20 wt % and fused silica. The two materials have absorption edges at 230 nm and 190 nm, respectively.
Figure 3:
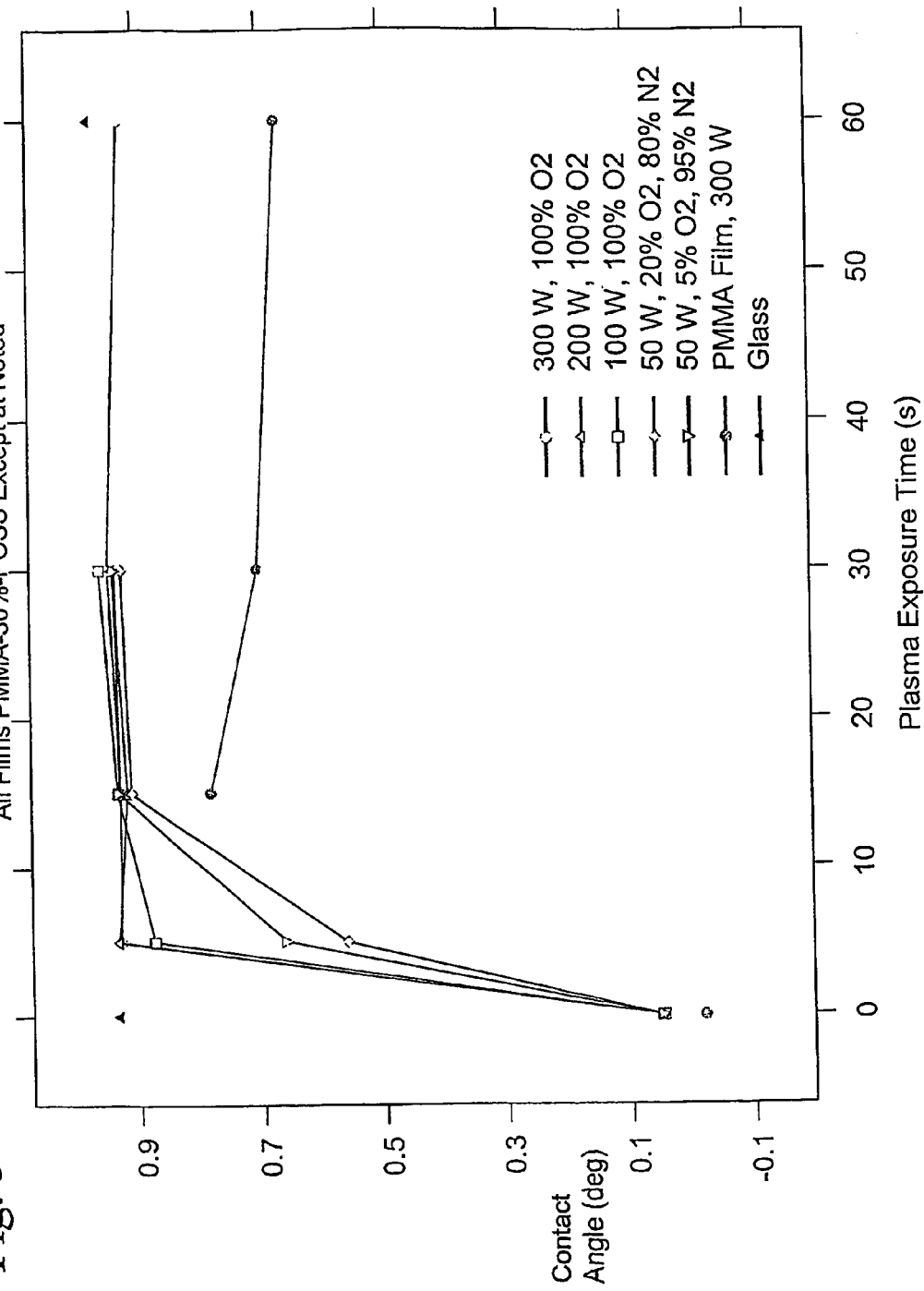
FIG. 3 Graphic display of water contact angle verse plasma exposure time.

As-deposited, the PMMA-POSS is not hydrophilic, nor does it become more hydrophilic with increasing POSS™ concentration, but O$_2$ plasma or UV ozone treatment of the PMMA-POSS polymer will enhance its hydrophilicity the stability of the hydrophilicity compared to pure PMMA (See FIG. 3). Thus the percentage of POSS™ in the polymer advantageously allows one to tune the resultant polymer to have the desired properties and modify the surface properties of the coated surface in the microdevices. By controlling the hydrophobicity/hydrophilicity of the surface, one can suppress unwanted binding of biomaterials on the surface. In addition, the presence of siloxal groups on the surface allows the charge on the surface to be adjusted by the concentration of POSS™ incorporated into the polymer used for bonding the microdevices. Furthermore, as shown in FIG. 2, the nanocomposite retained transparency with a POSS™ comonomer concentration of 20 wt %.

In accordance with one embodiment a microfluidic device is provided that has been coated with a POSS copolymer to improve the functional properties of the microdevice. These improved properties include optimizing electroosmotic flow, passivation of the substrate surface, decreasing thermal bonding temperatures for device manufacture and decreasing the surface roughness of microfluidic device interior surfaces. In one embodiment the improved microfluidic device comprises a body structure provided with a microchannel and an inlet port and an outlet port, wherein said inlet port and outlet port are formed on an exterior surface of said body structure and are in fluid communication with said microchannel, wherein the microchannel has an interior surface that is coated with a polymer of the present invention. The inlet port and outlet port can be formed on the same exterior surface or on two different surfaces of the body structure. In accordance with one embodiment the coating includes a polymer that comprises monomer units represented by the formula:

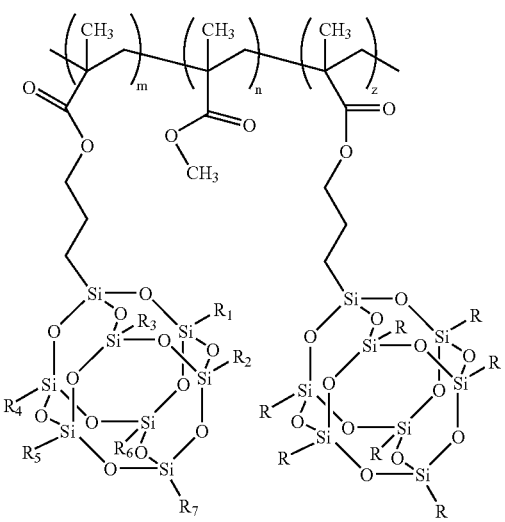

wherein R, $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of H and $C_1$-$C_4$ alkyl, m is 1, n is an integer ranging from 1 to 50 and z is 0 or 1. In one embodiment the coating may comprise a mixture of different POSS copolymers or in an alternative embodiment the coating consists essentially of a polymer that comprises monomer units represented by formula I.

In accordance with one embodiment the polymer of formula I is provided wherein z is zero and $R_1$, $R_2$, $R_3$, $R_4$, $R_5$, $R_6$, and $R_7$ are independently selected from the group consisting of $C_1$-$C_8$ alkyl, $C_2$-$C_8$ alkenyl, $C_2$-$C_8$ alkynyl, $C_1$-$C_8$ alkylcarboxyl, $C_1$-$C_8$ alkyl$(NR_{20}R_{21}R_{22})^+$, $C_1$-$C_8$ alkyl$(NR_{21}R_{22})$, $C_1$-$C_8$ alkyl$(NHR_{22})$, $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of $C_1$-$C_4$ alkyl, m is 1 and n is an integer ranging from 1 to 50. In another embodiment the polymer of formula I is used wherein z is zero and $R_1$, $R_2$, $R_3$, $R_4$, $R_5$, $R_6$, and $R_7$ are independently selected from the group consisting of $C_1$-$C_8$ alkyl, $C_2$-$C_8$ alkenyl, $C_2$-$C_8$ alkynyl, $C_3$-$C_8$ cycloalkyl, and $C_5$-$C_6$ aryl and in one embodiment, z is zero and $R_1$, $R_2$, $R_3$, $R_4$, $R_5$, $R_6$, and $R_7$ are independently selected from the group consisting of $C_1$-$C_4$ alkyl, and $C_5$-$C_6$ aryl. In an alternative embodiment a polymer of formula I is used wherein z is zero and $R_1$, $R_2$, $R_3$, $R_4$, $R_5$, $R_6$, and $R_7$ are all identical, and are selected from the group consisting of $C_1$-$C_8$ alkyl, $C_2$-$C_8$ alkenyl, $C_2$-$C_8$ alkynyl, $C_1$-$C_8$ alkylcarboxyl, $C_1$-$C_8$ alkyl $(N_{20}R_{21}R_{22})^+$, $C_1$-$C_8$ alkyl$(NR_{21}R_{22})$, $C_1$-$C_8$ alkyl$(NHR_{22})$, $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of $C_1$-$C_4$ alkyl, m is 1 and n is an integer ranging from 1 to 50, and in one embodiment $R_1$, $R_2$, $R_3$, $R_4$, $R_5$, $R_6$, and $R_7$ are all identical, and are selected from the group consisting of $C_1$-$C_4$ alkyl, $C_5$-$C_6$ cycloalkyl and phenyl. In accordance with another embodiment the polymer of formula I is provided wherein m and z are both 1, n is an integer ranging from 1-50, R is phenyl or $C_5$-$C_6$ cycloalkyl and $R_1$, $R_2$, $R_3$, $R_4$, $R_5$, $R_6$, and $R_7$ are each independently selected from the group consisting of $C_1$-$C_3$ alkyl. In another embodiment m and z are both 1, n is an integer ranging from 1-50, R is phenyl and $R_1$, $R_2$, $R_3$, $R_4$, $R_5$, $R_6$, and $R_7$ are each methyl.

Most polymer materials begin to absorb strongly around 300 nm, due to any conjugated carbon bonds, but the bonding structure in PMMA results in a much lower absorption edge. The optical properties of the PMMA-POSS copolymer were tested to see how the presence of the POSS™ moieties affected the absorption properties. Absorption spectroscopy data for an uncoated fused silica slide and a polymer coated fused silica slide are shown in FIG. 2. The thin film of PMMA-POSS exhibits optical transparency down to 230 nm. This compares favorably with the spectrum of the uncoated fused silica slide with an absorption edge of 190 nm. This UV transparency makes this a potentially attractive coating and bonding material for microdevices employing UV-visible detection, as many analytes of interest absorb in the 250-300 nm range.

The siloxal nature of the POSS™ portion of the polymer thin film should have properties similar to the siloxal groups on the surface of the glass itself. Because these siloxal groups are important in the generation of the EOF through a channel on a glass surface, this should also be true in the thin film coated channels in glass and other substrates (including for example various plastics). By controlling the percentage of POSS™ incorporated during preparation of the nanocomposite material, the number of siloxal groups in the resulting thin film coating the microfabricated channel can be adjusted. This will be very important in controlling the strength of the EOF within the channel. EOF is also affected by the surface roughness, thus the smoothing effect of the nanocomposite thin film on the microchannel walls will also be important in obtaining consistent and reproducible EOF movement in these channels.

In accordance with one embodiment the entire microfluidic device is prepared from the POSS copolymer. For example, any of the devices described herein can be prepared by polymerizing the PMMA-POSS polymer in the desired shape using standard injection mold or hot embossing techniques. In addition a microchannel bearing base comprised of a POSS copolymer can be bonded to a glass coverplate to provide an alternative embodiment of the present invention.

In one embodiment the POSS copolymers of the present invention are used as a bonding agent to bond either a silica based substrate to another silica based substrate, a plastic substrate to a plastic substrate or a silica based substrate to plastic substrate. In accordance with one embodiment a silica based substrate, such as a glass coverplate, is bonded to a plastic substrate. For example, the plastic substrate may comprise a polymer selected from the group consisting of PMMA, polycarbonate, polyethylene terephthalate, PMMA-POSS and other POSS copolymers. In another embodiment, the two substrates to be bound together both comprise silica compounds (for example both substrates being made of glass) but the two substrates have different thermal expansion properties relative to one another. These two embodiments are examples where the use of the POSS copolymers provides the maximum benefit as bonding agents. However the POSS copolymers can also be used in accordance with the present invention to bind two similar/identical glass substrates, or two similar/identical plastic substrates, to one another.

In accordance with one embodiment the method of using POSS copolymers to bind two substrates together comprises the steps of coating a first surface of the first substrate with a composition comprising a POSS copolymer, contacting the coated first surface of the first substrate with a first surface of a second substrate for a predetermined length of time; and heating the contacted surfaces to a maximum temperature ranging from about 100° C. to about 200° C. In one embodiment the contacted surfaces are heated to a temperature ranging from about 105° C. to about 140° C. Typically the first substrate will be biased towards/against the second substrate during the heating step to ensure adequate contact is made between the coated first surface and the first surface of the second substrate. The amount of pressure applied to bias the two substrates towards each other will vary based on the materials to be bonded, the bonding temperature and the duration of the applied pressure. However the typical pressures range from about 0.6 MPa to about 50 MPa, and more typically ranging from about 1.2 MPa to about 25 MPa (or about 180 psi to about 3600 psi).

In one embodiment the POSS copolymer polymer used to bond the two substrates together is produced by polymerizing a mixture comprising methylmethacrylate and a compound of the general structure:

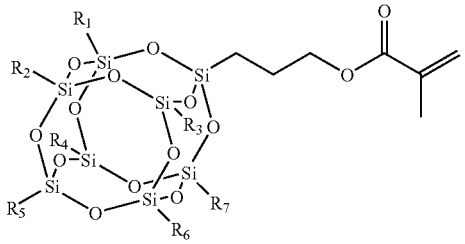

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl. In one embodiment the $R_1$, $R_2$, $R_3$, $R_4$, $R_5$, $R_6$, and $R_7$ substituents of the POSS™ moiety are all identical and are selected from the group consisting of $C_1$-$C_4$ alkyl, $C_5$-$C_6$ cycloalkyl, and $C_5$-$C_6$ aryl. In another embodiment $R_1$, $R_2$, $R_3$, $R_4$, $R_5$, $R_6$, and $R_7$ are each t-butyl.

In one embodiment both surfaces that are to be bonded to one another are coated with the POSS copolymer composition prior to the step of contacting the coated first surface of the first substrate with the coated first surface of the second substrate. In a further embodiment the surfaces to be bonded together are actively pressed together during at least a portion of the time while the two surfaces are heated. The biasing means used to hold the two surfaces in contact with one another can be any device known to those skilled in the art and includes but is not limited to clamps, weights, springs, screws, compression chambers and hydraulic/mechanical presses. Typically the two surfaces are pressed together under a force ranging from about 0.25 metric tons to about 5 metric tons [i.e. using pressure ranging from about 1.2 MPa to about 25 MPa (or about 180 psi to about 3600 psi)] for a predetermined length of time. The length of time will be varied based on the shape and the size of the surface area to be bonded. In accordance with one embodiment, at least one of the surfaces to be bonded is coated with a POSS copolymer composition and the two surfaces to be bonded are pressed together for a predetermined length of time, using a pressure ranging from about 1.2 MPa to about 25 MPa (or about 180 psi to about 3600 psi), while the two surfaces to be bonded are heated at a temperature ranging from about 105° C. to about 140° C. for at least a portion of the time the two substrates are pressed together.

The coating of the POSS copolymer composition can be applied to the substrates of the present invention using any standard technique including spraying, dipping and spin coating. The coating is typically applied as a continuous film having an average thickness of about 0.1 to about 3.0 μm. In one embodiment the film has an average thickness of about 0.5 to about 2 μm.

In accordance with one embodiment of the present invention a microfluidic device is provided wherein a silica based substrate is bound via a POSS copolymer to base, wherein the base is provided with one or more microchannels that have their interior surfaces coated with a composition comprising a POSS copolymer of the present invention. In one embodiment the silica based substrate is a glass coverplate and the base is a glass or plastic substrate that comprises a microchannel. In accordance with one embodiment a glass microfluidic device is prepared by etching microchannels into a glass plate, coating the etched glass plate with a POSS copolymer using a spin coating procedure, and permanently bonding a glass coverplate to the etched surface using moderate temperatures (about 105° C. to about 140° C.) and a compression bonding step. In an alternative embodiment the coverplate is coated with the polymer (rather than the etched glass surface) and bonded to the etched surface.

In one embodiment the etched surface but not the interior surface of the microchannels is coated with the POSS copolymer using standard masking techniques. Alternatively, in another embodiment, the spin coating procedure also coats the etched features within the glass plate with a thin layer of the PMMA-POSS material. This coating tends to smooth the surface of the etched channel in the glass, with atomic force microscopy (AFM) revealing a significant reduction in the surface roughness. Because this polymeric coating remains through the bonding process, this should lead to improved fluid flow dynamics and less surface adsorption in the microfluidic channels. In addition, the nature of the surface is now modified to reflect the nature of the polymeric material. By adjusting the amount of POSS™ used in the preparation of the copolymer, in conjunction with an $O_2$ plasma or UV ozone treatment, the hydrophilicity of the surfaces within the microchip can be selected. This can be used to alter the binding properties of the glass for proteins and other biomolecules, and control the strength of the EOF generated within microchannels. In addition to its bonding and coating properties, the PMMA-POSS material has been selected for its optical properties to insure that it does not interfere with detection during the normal analyses carried out in glass microdevices.

In accordance with one embodiment a microfluidic device is provided comprising a base wherein the base comprises a microchannel, an inlet port and an outlet port, wherein the inlet port and outlet port are formed on an exterior surface of said base and are in fluid communication with said microchannel and the interior surface of the microchannel is coated with a POSS copolymer. In one embodiment the inlet port and the outlet port are both formed on the same exterior surface and the interior surfaces of the microchannel, inlet port and outlet port are coated with PMMA-POSS.

The POSS copolymer modified microfluidic devices of the present invention can be prepared in accordance with one embodiment by bonding a silica based coverplate to a base, wherein said coverplate comprises a first and second port, and the base comprises a microchannel. In this embodiment the silica based coverplate is bonded to the base, in an orientation that places the first and second ports of the coverplate in fluid communication with the microchannel. However, in an alternative embodiment one end of the microchannel is provided with an outlet port, formed on a surface other than that where the inlet port is formed. Thus an inlet port is formed on a first surface of the base and in communication with the microchannel wherein the outlet port is formed on a second surface of the base and in fluid communication with the microchannel. In this embodiment the silica based coverplate contains only one port that is aligned with the inlet port when the coverplate is bound to the base. Alternatively, in certain diagnostic applications of the microfluidic device an outlet port may not be required. Therefore, in this embodiment the base includes a microchannel formed on an exterior surface of said base and a silica based coverplate bound to the microchannel bearing surface, wherein the coverplate comprises a port that is aligned to be in fluid communication with the microchannel when the coverplate is bound to the base.

To bind the silica based coverplate to the base, a surface of the coverplate and/or the microchannel bearing surface of the base is coated with a composition comprising a polymer produced by polymerizing a mixture comprising methylmethacrylate, and a compound of the general structure:

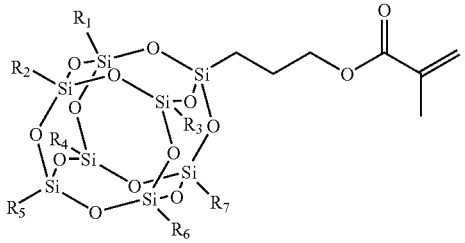

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl. In one embodiment $R_1$, $R_2$, $R_3$, $R_4$, $R_5$, $R_6$, and $R_7$ are identical and selected from the group consisting of $C_1$-$C_6$ alkyl, $C_5$-$C_6$ cycloalkyl and $C_5$-$C_6$ aryl. In one embodiment the polymer used to coat the surface of the coverplate and/or base comprises monomer units represented by the formula

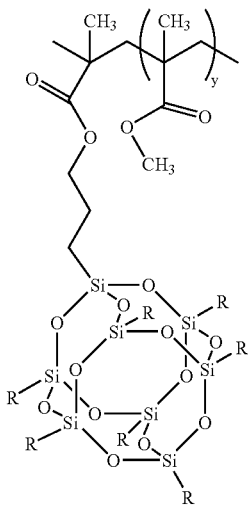

wherein y is an integer ranging from about 1 to about 50 and R is selected from the group consisting of $C_1$-$C_4$ alkyl, $C_5$-$C_6$ cycloalkyl, and $C_5$-$C_6$ aryl. The coverplate is positioned to have an optionally coated external surface in contact with the optionally coated microchannel bearing surface of the base, wherein either the coverplate or the base or both surfaces are coated with the polymer. The coated surface of the coverplate and/or the base are then biased towards/against one another for a predetermined length of time. In one embodiment the coverplate and the base are pressed together at a pressure ranging from about 4 MPa to about 24.5 MPa. The coverplate and the base are held in contacted for a predetermined length of time while the contacted surfaces are heated a temperature ranging from about 100° C. to about 200° C. (more typically ranging from about 105° C. to about 140° C.) to bind the base to the coverplate via the POSS copolymer.

The microchannel of the device can also be coated with a POSS copolymer of the present invention. In one embodiment, the microchannel is coated with the same polymer that is used to bond the coverplate to the base. Alternatively, in one embodiment a different POSS copolymer is selected for binding relative to that selected for coating the microchannel. In this embodiment the POSS copolymer used for binding the two substrates can be selected based on its optimal binding properties whereas the POSS copolymer used to coat the microchannel can be selected based on its optimal chromatographic properties. In one embodiment the inner surfaces of the microchannels formed in the base are coated only with a second "chromatography optimized" POSS copolymer. This coating step can take place either before or after the coverplate is bound to the base. If the coating is applied to the microchannel interior surfaces after binding of the coverplate to the base (and thus after the heating step), the formed microchannel can be optionally flushed with a strong acid or base (to regenerate the hydroxyl groups on the silanols) prior to applying a coating of the second POSS copolymer. For example the microchannel can be flushed with a solution comprising NaOH, HCl or $HNO_3$. Furthermore, if during the construction of the microdevice the microchannel interior surfaces were coated with a POSS copolymer that does not have the desired optimal chromatographic properties, that POSS copolymer can be removed by the use of solvents prior to coating the surface of the microchannel with the desired POSS copolymer. Suitable solvents for such use include, but are not limited to, standard organic solvents such as acetone, THF (tetrahyrdofuran), chloroform, hexane and toluene. For example, the microchannel can be flushed with the solvent, followed by flushing with a basic or acidic solution and then flushed with a solution comprising the desired POSS copolymer.

In accordance with one embodiment the inner surface of the microchannel is coated with a POSS copolymer produced by polymerizing a mixture comprising methylnethacrylate, and a compound of the general structure:

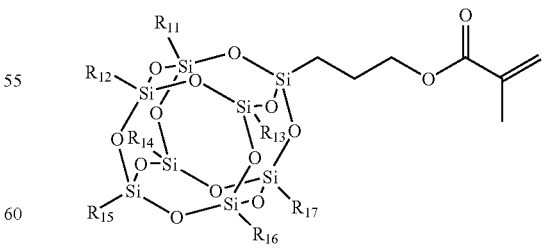

wherein $R_{11}$, $R_{12}$, $R_{13}$, $R_{14}$, $R_{15}$, $R_{16}$, and $R_{17}$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl$(NR_{20}R_{21}R_{22})^+$, $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of H and $C_1$-$C_4$ alkyl. In one embodiment $R_{11}$, $R_{12}$, $R_{13}$, $R_{14}$, $R_{15}$, $R_{16}$, and $R_{17}$ are independently selected from the group consisting of $C_1$-$C_{18}$ alkyl, $C_1$-$C_8$ alkylcarboxyl, $C_1$-$C_8$ alkylsulfate, $C_3$-$C_8$ cycloalkyl and $C_5$-$C_6$ aryl.

The PMMA-POSS bonding procedure is also applicable to plastic materials. The present invention provides, among other things, a novel method for bonding of plastic microdevices, but also provides a method for controlling the surface of the structures within the microdevice. As with the glass devices, this will allow control of the strength of the EOF by changing the composition of the copolymer used to form the thin film coating.

One embodiment of the present invention is directed to a hybrid microfluidic device comprising a coverplate bonded to a base wherein the coverplate is composed of different materials than that of the base. In one embodiment both the coverplate and the base are constructed from glass, but the glass of the coverplate has different thermal expansion properties relative to the glass used to manufacture the base. In another embodiment the coverplate comprises a silica based substrate such as glass, and the base is formed from a thermoplastic polymer, including for example, a PET, PMMA, POSS copolymer or polycarbonate component. In this embodiment the two components of the hybrid device are bound to one another through a polymer film, whereas the polymer film comprises a repeating subunit represented by the general structure:

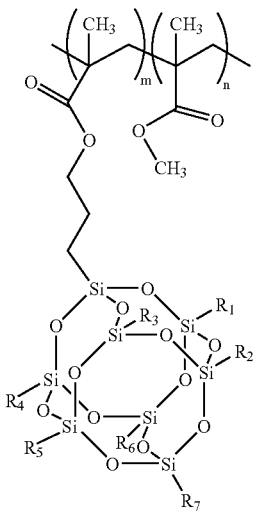

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl and $C_5$-$C_6$ aryl, and m is 1 and n is an integer ranging from 1 to 50. In one embodiment $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl, m is 1; and n is an integer ranging from 1 to 50. In another embodiment $R_1$, $R_2$, $R_3$, $R_4$, $R_5$, $R_6$, and $R_7$ are identical and selected from the group consisting of $C_1$-$C_3$ alkyl.

In accordance with one embodiment, a microfluidic device is provided with one or more microchannels and an inlet port and an outlet port, wherein said inlet port and outlet port are formed on an exterior surface of said body structure and are in fluid communication with said microchannel. The microchannel of the hybrid device has an interior surface that is coated with a polymer comprising monomer units represented by the formula:

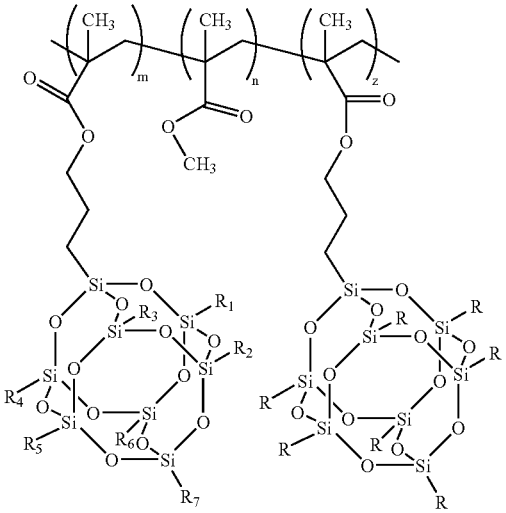

wherein R, $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of H and $C_1$-$C_4$ alkyl, m is 1, n is an integer ranging from 1 to 50 and z is 0 or 1.

In one embodiment the hybrid device comprises a first silica based component bound to a second thermoplastic polymer comprising component. More particularly, in one embodiment, a first component is provided that is formed from silica based material, wherein the first component comprises a first microchannel, an inlet port and an outlet port, wherein said inlet port and outlet port are formed on an exterior surface of said first component and in fluid communication with said first microchannel. In one embodiment, the inlet port and outlet port are formed on different exterior surfaces of the first component. The second thermoplastic polymer comprising component of the hybrid device comprises a second microchannel having a first and second end, wherein the first end of the second microchannel is in fluid communication with the outlet port of the first component, and the second end of the second microchannel is in fluid communication with the exterior surface of the second component. Such a hybrid device could take advantage of glasses' superior properties for processing/purifying nucleic acid sequences as well as plastic's superior properties for allowing rapid thermal cycling necessary for conducting PCR reactions.

The PMMA-POSS bonding methodology of the present invention provides a novel way to reliably bond glass devices at moderate temperatures, as well as an additional method for bonding plastic substrates, thus allowing for an easily implemented method to form hybrid devices. The simple nature of the bonding process also greatly reduces the production time for fabrication of microfluidic devices, particularly with glass substrates. Due to its success in reducing the roughness of etched glass surfaces, the material may be capable of increasing the resolution of separations on a chip by reducing the surface area and increasing fluid flow. The surface coating imparted by the bonding procedure to microfabricated structures within the device also provides a method for generating and controlling the EOF. The optical properties of the PMMA-POSS material make it compatible with most of the normally employed detection methods.

EXAMPLE 1

Use of PMMA-POSS in Glass Microchip Bonding
   Coating Procedure and Analysis of Coating.
   A uniform coating of PMMA-POSS 20 wt % thin film was obtained via spin-coating a solution of the polymeric material onto etched and unetched borofloat glass plates. AFM examination of the surfaces showed a uniform coating of the surfaces both outside and within the microfabricated channel. Table 1 contains the AFM data for an unetched substrate and an etched channel after coating with the PMMA-POSS 20 wt % material. The unetched surface is very smooth while the etched channel exhibits a rough surface due to the etching process. A control sample with no polymer film showed an average roughness of 6.797 nm inside of the channel, indicating that the PMMA-POSS actually smoothes the etching process by a factor of 3 compared to the as-etched sample. This is particularly important, because the surface area inside the channel is much higher in the as-etched sample as indicated in Table 1. This high surface area will result in a higher probability of enzyme adsorption and a profound change in the fluid dynamics of the liquids in the microfluidic channels. Both of these are serious problems with microfluidic structures.

TABLE 1

| Sample | Average Roughness | Surface Area |
|---|---|---|
| As received | 2.314 nm | 100.51 µm² |
| No etch-20 wt % PMMA-POSS | 0.678 nm | 100.05 µm² |
| Etched channel-no film | 6.797 nm | 100.96 µm² |
| Etched-20 wt % PMMA-POSS | 0.370 nm | 100.02 µm² |
| Etched channel-20 wt % PMMA-POSS | 2.264 nm | 100.03 µm² |

Bonding Procedure
   PMMA-POSS thin films are deposited on both the microfabricated surface and the coverplateplate. The two surfaces are then annealed at 150° C. at a pressure of 4.4 MPa. Bonding was shown to be successful by the lack of bifringence between the glass plates and the ability to flow liquid through the microfabricated channel using capillary action. No liquid was observed to leak between the plates. The bonding temperature is above the glass transition temperature of the copolymer, thus the exact nature of the surface within the microchannel is not yet known.
   Glass/Glass Hybrids
   Thermal bonding requires the use of etched plates and coverplate plates with exactly the same thermal expansion properties, otherwise the glass will shatter as it cools and contracts to different extents. The low temperature bonding method using the PMMA-POSS nanocomposite will eliminate this problem since the glass is not bonded to itself, and since the temperature change experienced by the glass is greatly reduced. This method allows dissimilar glass devices to be prepared, taking advantage of the better etch properties of some glasses, and the ability to select a coverplate with the optimum properties.

EXAMPLE 2

Use of PMMA-POSS in Controlling EOF in Non-Glass Substrates
   The PMMA-POSS bonding procedure is applicable to a variety of microchip substrates other than glass. Fused silica or quartz microchips will be required for both UV absorbance and UV fluorescence detection methods. These materials require very high temperatures for bonding, thus the low temperature compression bonding method will be important for these devices. As stated above, the optical properties of the POSS copolymer nanocomposite materials do not interfere with UV detection methods.
   This bonding method can also be used to fabricate microchips out of plastic materials. These materials, for use in the next generation of disposable devices, can be easily and cheaply fabricated. Bonding by other methods is possible, but this bonding method offers the additional advantage of coating the microfabricated structures at the same time. Unlike glass, most plastic materials will not have charged surfaces capable of generating EOF after fabrication. To generate an EOF, the surface has to be treated to form ionic species on the surface. The use of the PMMA-POSS bonding method eliminates the need for additional processing steps, and forms a surface on the microdevice structures that should generate EOF in these devices.
   It will also be possible to fabricate hybrid devices using this bonding method. These devices can involve different types of plastics, or plastic and glass or quartz devices. Fabrication in plastic has the advantage of cost of fabrication and high aspect ratios, but the optical properties are not always ideal. By bonding a glass or quartz coverplate to a plastic microchip base, the detection system can be designed using its optimal substrate while the fabrication is carried out on a second substrate material. Hybrid devices also allow the optimal substrate to be used for each processing step in integrated microdevices. Integrated clinical devices, for example, require PCR amplification and electrophoretic separations on the same device. While glass microdevices perform best for the separations, plastic microchips have advantages for the amplification reaction. The hybrid device required to integrate these two steps is very difficult to fabricate with current bonding methods.

EXAMPLE 3

Oxygen Plasma Treatment of PA-POSS-Coated Surfaces to Tune the Hydrophobic/Hydrophilic Character
   One of the characteristics of thin films of PMMA-POSS [a copolymer nanocomposite blend of polymethylmethacrylate (PMMA) and polyhedralsilsequioxane (POSS)] that make them attractive for use in microdevices is the ability to control their physicochemical properties, specifically, their hydrophobic/hydrophilic character. This can be accomplished by simply altering the amount of POSS™ present with the PMMA, but the exposure of the POSS™ to the surface may ultimately control the extent to which the POSS™ enhances hydrophilicity. This effect can be enhanced by oxygen plasma treatment of the PMMA-POSS surface which appears to enhance the hydrophilicity of the surface (based on an increase in contact angle with water). Plasma oxidation of hydrophobic surfaces, in general, increases hydrophilicity, however, this effect is exacerbated in the presence of POSS, with the plasma oxidation most likely increasing the exposure of POSS™ on the surface—this enhances the hydrophilic character above that of PMMA.
   One way in which modification of the surface chemistry of the thin films can be monitored is to use contact angle measurements of deionized water. Comparison a thin film of PMMA with a copolymer nanocomposite blend of PMMA and 30% POSS™ was conducted in which the contact angle was measured for surfaces treated with the different polymers. The cosine of the contact angle produced for various plasma treatments was determined to be a function of exposure time in the plasma. A cosine less than or equal to 1.0 would represent a completely hydrophilic surface in which the water completely wets the surface forming no angle. A cosine approximately equal to zero represents a highly hydrophobic surface. All of the surfaces used in the experiment were glass microscope slides treated with a 20 minute "Piranha Clean" (70% conc. $H_2SO_4$: 30% conc. $H_2O_2$ @ 95° C.), rinsed in deionized water, dried in compressed nitrogen, and stored in a nitrogen dry box for no more than two days. The glass surface, as-prepared, is highly hydrophilic. Spun-cast films of pure PMMA (high molecular weight dissolved in THF), PMMA-20%-POSS and PMMA-30%-POSS all are highly hydrophobic as-deposited.

Plasma experiments were performed in a March Instruments PX-250 plasma tool operating in a direct plasma mode. Plasma conditions of exposure time, power and percentage of oxygen were varied and controls were performed on pure PMMA thin films and glass substrates that did not receive a film deposit. An oxygen plasma at 300, 200 and 100 Watts and 100% oxygen flowing into the chamber resulted in the conversion of the PMMA-POSS thin films from hydrophobic to hydrophilic in less than 5 seconds (See FIG. 3). Pure PMMA thin films are considerably more hydrophilic under the same conditions at 300 W, 100% $O_2$ for 60 s than the unexposed thin films, but they do not completely wet the surface. Lowering the plasma power to 50 W and reducing the amount of oxygen present in the chamber by varying the ratio of oxygen to an inert carrier gas such as nitrogen allows for tuning of the hydrophilicity of a PMMA-30%-POSS thin film exposed for 5 s at 50 W in a 20% $O_2$:80% $N_2$ ambient. Use of a remote rather than a direct plasma will enable better control of the transition between hydrophobic and hydrophilic as a remote plasma is designed to allow less chemically and physically energetic gaseous species to diffuse to the surface being treated.

The invention claimed is:
1. A method of preparing a microfluidic device said method comprising the steps of
providing a silica based coverplate, wherein said coverplate comprises a first and second port, and a base, wherein said base comprises a microchannel;
coating a surface of the silica based coverplate or the microchannel bearing surface of the base with a first composition comprising a polymer produced by polymerizing a mixture comprising methylmethacrylate, and a compound of the general structure:

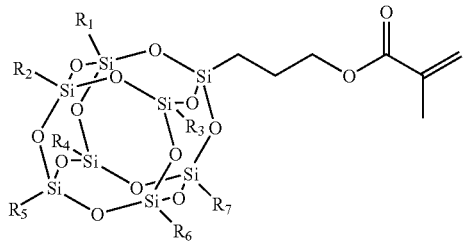

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl;
contacting the silica based coverplate with the microchannel bearing surface of the base, for a predetermined length of time, in an orientation that places the first and second ports of the coverplate in fluid communication with the microchannel and places the coated surface between the coverplate and the base;
heating the contacted surfaces to a temperature ranging from about 100° C. to about 200° C.; and contacting the inner surface of the microchannel with a second composition comprising a polymer produced by polymerizing a mixture comprising methylmethacrylate, and a compound of the general structure:

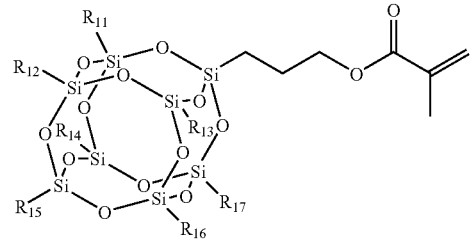

wherein $R_{11}$, $R_{12}$, $R_{13}$, $R_{14}$, $R_{15}$, $R_{16}$, and $R_{17}$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl($NR_{20}R_{21}R_{22}$)$^+$, $C_1$-$C_8$ alkyl($NR_{21}R_{22}$), $C_1$-$C_8$ alkyl($NHR_{22}$), $C_1$-$C_8$ alkylsulfate, $C_3$-$C_8$ cycloalkyl, and $C_5$-$C_6$ aryl, wherein $R_{20}$, $R_{21}$ and $R_{22}$ are independently selected from the group consisting of $C_1$-$C_4$ alkyl.

2. The method of claim 1, wherein $R_{11}$, $R_{12}$, $R_{13}$, $R_{14}$, $R_{15}$, $R_{16}$, and $R_{17}$ are independently selected from the group consisting of $C_1$-$C_8$ alkyl, $C_2$-$C_8$ alkenyl, $C_2$-$C_8$ alkynyl, $C_3$-$C_8$ cycloalkyl, and $C_5$-$C_6$ aryl.

3. The method of claim 1, further comprising the step of contacting the inner surface of the microchannel with an organic solvent after the heating step and prior contacting the microchannel with said second composition.

4. A hybrid microfluidic device, said device comprising
a silica based component; and
a polymer component, wherein the silica based component is bonded to the polymer component through a polymer film comprising a repeating subunit represented by the general structure:

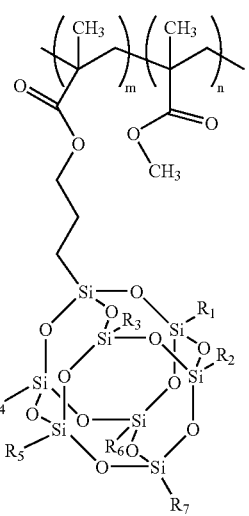

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl;
m is 1; and
n is an integer ranging from 1 to 50.

5. The hybrid device of claim 4, wherein the silica component comprises a coverplate and the polymer component comprises a body structure formed by said polymer, wherein the body structure is provided with a microchannel and an inlet port and an outlet port, wherein said inlet port and outlet port are formed on an exterior surface of said body structure and are in fluid communication with said microchannel, and said microchannel has an interior surface that is coated with a polymer comprising monomer units represented by the formula:

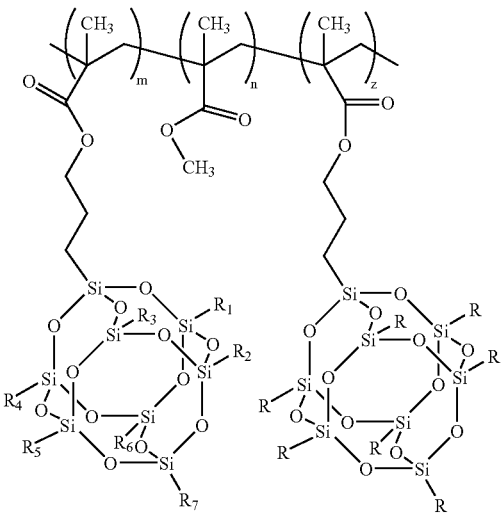

wherein R, $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkyl$(NR_{21}R_{22})$, $C_1$-$C_8$ alkyl $(NHR_{22})$, $C_1$-$C_8$ alkylsulfate, $C_3$-$C_8$ cycloalkyl, and $C_5$-$C_6$ aryl;

m is 1;

n is an integer ranging from 1 to 50 and z is 0 or 1.

6. The hybrid device of claim 5, wherein said coverplate is provide with two ports that are aligned with the inlet and outlet ports to allow fluid communication between the microchannel and the exterior surface of the device.

7. The hybrid device of claim 4, wherein the silica component comprises a first body structure formed from silica oxide, wherein the first body structure is provided with a first microchannel and an inlet port and an outlet port, wherein said inlet port and outlet port are formed on an exterior surface of said first body structure and are in fluid communication with said first microchannel, and said polymer component comprises a second body structure formed by said polymer, wherein the second body structure is provided with a second microchannel having a first and second end, wherein the first end of the second microchannel is in fluid communication with said outlet port and the second end of the second microchannel is in fluid communication with the exterior surface of said second body structure.

8. The hybrid device of claim 7, wherein the polymer comprising the second body structure is a polymer produced by polymerizing a mixture comprising methylmethacrylate, and a compound of the general structure:

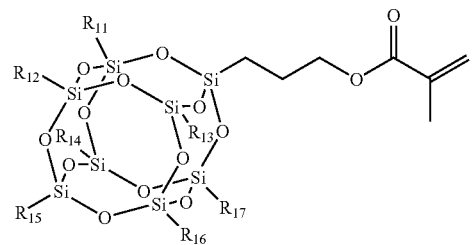

wherein $R_{11}$, $R_{12}$, $R_{13}$, $R_{14}$, $R_{15}$, $R_{16}$, and $R_{17}$ are independently selected from the group consisting of $C_1$-$C_{18}$ alkyl, $C_2$-$C_{18}$ alkenyl, $C_2$-$C_{18}$ alkynyl, $C_3$-$C_8$ cycloalkyl, and $C_5$-$C_6$ aryl.

9. The hybrid device of claim 7, wherein the polymer comprising the second body structure is selected from the group consisting of PET, PMMA and polycarbonate.

10. The hybrid device of claim 7, wherein the inner surface of the second microchannel is coated with a polymer comprising monomer units represented by the formula:

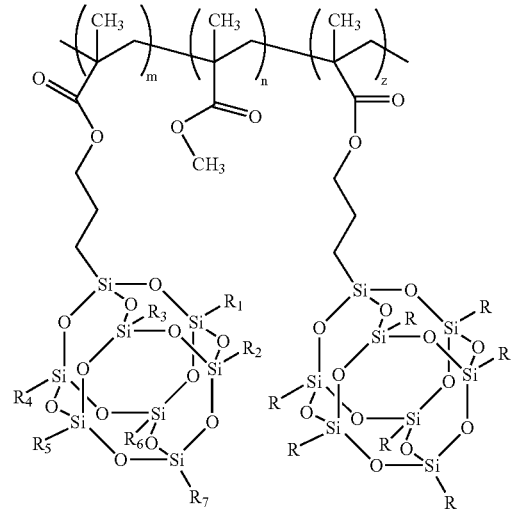

wherein R, $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkyl$(NR_{21}R_{22})$, $C_1$-$C_8$ alkyl $(NHR_{22})$, $C_1$-$C_8$ alkylsulfate, $C_3$-$C_8$ cycloalkyl, and $C_5$-$C_6$ aryl;

m is 1;

n is an integer ranging from 1 to 50; and z is 0 or 1.

11. A microfluidic device comprising a first substrate bound to a second substrate via a POSS copolymer wherein the second substrate is provided with a first microchannel and an inlet port and an outlet port, wherein said inlet port and outlet port are formed on an exterior surface of said first substrate and are in fluid communication with said first microchannel.

12. The device of claim 11, wherein the first substrate comprises a glass coverplate.

13. The device of claim 12, wherein the second substrate is comprised of glass having different thermal expansion properties than the glass comprising the coverplate.

14. The device of claim 12, wherein the second substrate is comprised of a thermoplastic polymer.

15. The device of claim 14, wherein the thermoplastic polymer is PMMA or a POSS copolymer.

16. The device of claim 11, wherein the first substrate and second substrate are both comprised of a thermoplastic polymer.

17. The device of claim 16, wherein said first substrate is provided with a second microchannel having a first and second end, wherein the second end of the second microchannel is in fluid communication with said outlet port of the second substrate and the first end of the second microchannel is in fluid communication with an exterior surface of said second substrate.

18. The device of claim 17 wherein the first and second microchannels are coated with a POSS copolymer produced by polymerizing a mixture comprising methylmethacrylate, and a compound of the general structure:

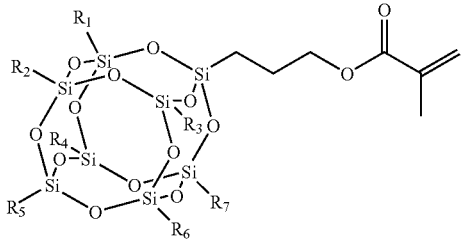

wherein $R_1$, $R_2$, $R_3$, $R_4$, $R_5$, $R_6$, and $R_7$ are independently selected from the group consisting of $C_1$-$C_{18}$ alkyl, $C_2$-$C_{18}$ alkenyl, $C_2$-$C_{18}$ alkynyl, $C_1$-$C_8$ alkylcarboxyl, $C_1$-$C_8$ alkyl $(NR_{20}R_{21}R_{22})^+$, $C_1$-$C_8$ alkyl$(NR_{21}R_{22})$, $C_1$-$C_8$ alkyl $(NHR_{22})$, $C_1$-$C_8$ alkylsulfate, $C_3$-$C_8$ cycloalkyl, and $C_5$-$C_6$ aryl.

19. The device of claim 11, 14 or 17 wherein the POSS copolymer is a polymer produced by polymerizing a mixture comprising methylmethacrylate, and a compound of the general structure:

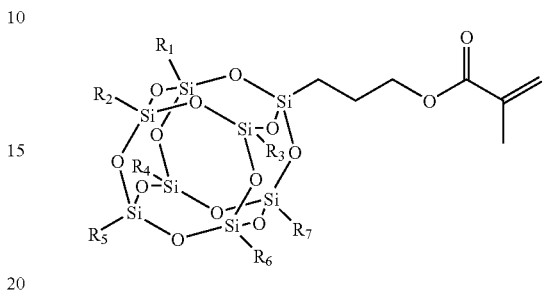

wherein $R_1$, $R_2$, $R_3$, $R_4$, $R_5$, $R_6$, and $R_7$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_5$-$C_6$ aryl.

* * * * *